United States Patent [19]

Chodkiewicz

[11] 4,032,534
[45] June 28, 1977

[54] CERTAIN 2-(2-THIOETHYL)THIAZOLIDINE-4-CARBOXYLIC ACIDS

[75] Inventor: Marc X. Chodkiewicz, Feucherolles, France

[73] Assignee: Ferlus-Chimie S.A., Cournon D'Auvergne, France

[22] Filed: Jan. 28, 1976

[21] Appl. No.: 653,093

Related U.S. Application Data

[63] Continuation of Ser. No. 451,410, March 15, 1974, abandoned.

[30] Foreign Application Priority Data

Mar. 22, 1973 France .............................. 73.10266

[52] U.S. Cl. ................. 260/306.7 C; 260/294.8 C; 260/599; 260/601 R; 424/263; 424/270
[51] Int. Cl.² ....................................... C07D 277/06
[58] Field of Search ............................ 260/306.7 C

[56] References Cited

OTHER PUBLICATIONS

Elderfield (ed.), Heterocyclic Compounds, vol. 5, John Wiley & Sons, N.Y.C., 1957, pp. 697–700.
Noller, Chemistry of Organic Compounds, Saunders, Philadelphia, 1965, p. 841.

Primary Examiner—R. Gallagher
Attorney, Agent, or Firm—McDougall, Hersh & Scott

[57] ABSTRACT

The invention concerns new compounds for use in the pharmaceutical industry, its subject-matter being (thio-2-ethyl)-2 carboxy-4 thiazolidinic compounds of the general formula:

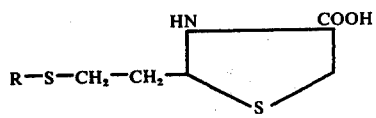

where R is selected from hydrogen atom, alkyl, phenyl, alkylaryl and acyl radicals, heterocyclic groups such as pyridoxazole or benzimidazole, and alkyl- carboxylic groups, particularly acetic, and esters and amide derivatives thereof, and salts of addition of the compounds. These compounds are of use in the production of medicines with analgesic and mucolytic properties.

8 Claims, No Drawings

CERTAIN 2-(2-THIOETHYL)THIAZOLIDINE-4-CARBOXYLIC ACIDS

This application is a continuation of application Ser. No. 451,410 filed Mar. 15, 1974, and now abandoned.

The present invention relates to 2-(2'-thioethyl)-4-carboxy thiazolidinic derivatives, and a process for their preparation. It also relates to medicines using these compounds as active constituents.

The compounds according to the present invention are 2-(2'-thioethyl)4-carboxy thiazolidinic derivatives having the general formula I:

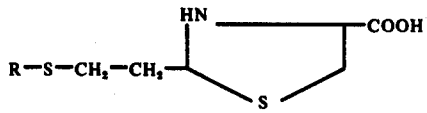

in which:

R is selected from a hydrogen atom; an alkyl radical such as $CH_3$, $C_2H_5$ or $C_{12}H_{25}$; a phenyl radical, which may or may not be substituted in the ortho and/or meta and/or para position by a substituent selected from halogen atoms, lower alkyl radicals, alkoxy radicals and nitro radicals;

an alkylaryl radical of the formula:

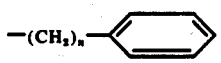

in which n is 1, 2 or 3, and the aromatic nucleus may or may not be substituted in the ortho and/or meta and/or para position, by a substituent selected from halogen atoms, lower alkyl radicals, alkoxy radicals and nitro radicals;

an acyl radical of the formula $-CO-R_1$, in which $R_1$ represents an alkyl radical;

A heterocyclic group of the formula $-(CH_2-)_n -R_2$, in which $n'$ is 0, 1 or 2, and $R_2$ is a heterocyclic radical such as pyridoxazole, or purine, or guanine, or benzimidazole, which may or may not be substituted, on the benzene nucleus, by a substituent selected from lower alkyl radicals, nitro group, halogen atoms such as F, Cl, Br, and alkoxy radicals such as $OCH_3$, $OC_2H_5$, and a group of the formula

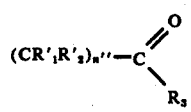

in which:

$n''$ is 1, 2 or 3, $R'_1$ and/or $R'_2$ represent a hydrogen atom or a lower alkyl radical, $R_3$ represents a group selected from a) a hydroxy group, in which case the derivative of the present invention is a 4-carboxy 2-thiazolidinyl 2-ethyl mercapto alkyl carboxylic acid, which may be in the form of a salt, particularly with one of the organic bases such as diisopropylamine, or with an amino acid such as arginine;

b. an alkoxy group of the formula $-OR_4$, in which case the derivative of the invention is an ester of a 4-carboxy 2-thiazolidinyl 2-ethyl mercapto alkylcarboxylic acid with an aliphatic, alicyclic, aromatic or heterocyclic alcohol, $R_4$ representing a lower alkyl, cycloalkyl or phenyl radical, which may or may not be substituted in the ortho and/or meta and/or para position by a halogen atom or an arylalkyl or heterocyclic radical, and c. an amine group of the formula $-NH-R_5$, in which case the derivative of the invention is an amide of a 4-carboxy 2-thiazolidinyl 2-ethyl mercapto alkylcarboxylic acid with a primary or secondary aliphatic, aromatic or heterocyclic amine, $R_5$ representing an alkyl, cycloalkyl or phenyl radical, which may or may not be substituted, or a heterocyclic radical.

Compounds according to the formula (I) may likewise be in the form of salts of addition with mineral or organic bases. A lower alkyl radical generally comprises from 1 to 5 carbon atoms, whereas a higher alkyl radical comprises more than 5, and preferably from 5 to 15 carbon atoms.

The compounds of the present invention are products useful in pharmacology. They have analgesic and mucolytic properties which render them useful as medicines in the treatment of conditions of the respiratory mucous membrane; these medicines are particularly indicated in pneumology for bronchitis and tracheobronchitis, and in ortho-rhino-laryngology for pharyngitis, rhinopharyngitis, otitis and sinusitis.

In addition, certain of the compounds of the present invention have hypotensive, anti-hypertensive, and cardiostimulative properties, which render them useful as medicines in the therapeutic treatment of cardiovascular conditions.

Further according to the present invention there is provided a method of preparing a 2-(2-thioethyl)-4-carboxy-thiazolidinic derivative comprising reacting acrolein with a compound of the formula R-SH wherein R is as defined hereinabove to form an aldehyde, and condensing the aldehyde with cystein or chlorhydrate of cystein.

The method may advantageously be carried out in two stages in the following way:

1. The first stage consists in adding a free compound of the general formula R-SH to acrolein. A reaction takes place at a temperature of between 0 and 5° C in the presence of triethylamine, and is generally conducted in ethanol or ether. The reaction may be represented as:

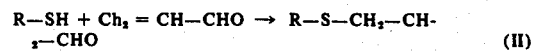

R being as defined hereinabove.

2. The second stage is intended to create the thiazolidinic cycle. In order to do this, chlorohydrate of cystein in hydroalcoholic solution is condensed, at ambient temperature, with the aldehyde of the formula (II) previously obtained. The reaction is as follows:

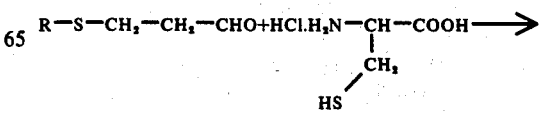

-continued

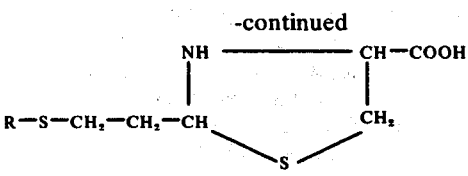

The reaction may advantageously be carried out in the presence of potassium acetate.

The thiazolidinic derivative obtained may be isolated, and purified by recrystallisation in degasified water or in absolute alcohol. If necessary, it may be reacted again with an amine in order to obtain the corresponding salt of addition.

Embodiments of the present invention will now be described by way of illustration in the following Examples. The nature of the particular compounds whose preparation is described is set out in table I.

EXAMPLE 1

4-carboxy-thiazolidinyl-2-ethyl mercapto acetic acid.

(Table I: compound No. 4)

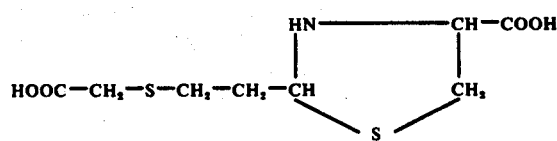

Into a 1000ml reactor fitted with an agitator, a bromine ampoule and a nitrogen blower, there was introduced 66.82 ml (1 mole) of freshly-distilled acrolein in solution in 150ml of absolute alcohol. The reactor was kept at 0° C by a refrigerating mixture, and was agitated under nitrogen. 1 mole of triethylamine salt of thioglycolic acid (prepared previously by the cold action of 1 mole of triethylamine on 1 mole of thioglycolic acid in 150ml of absolute alcohol) was added drop by drop.

When the addition was completed, the resulting mixture was agitated for one hour at ambient temperature, and then an alcoholic solution of cystein chlorhydrate (1 mole (157g) in 200 ml of alcohol at 95° C) was introduced. A precipitate rapidly formed. The mixture was left for one night under nitrogen, after which the precipitate was filtered off and washed in water and alcohol. The precipitate was recrystallised in boiling water under nitrogen, and then dried in a drier, away from light. F (Kofler) = decomposition from 186° C.

EXAMPLE II 4-carboxy thiazolidinyl 2-ethyl mercapto acetate of di(diisopropylamine)

(Table I: compound No. 5)

This derivative was obtained by the reaction of 2 moles of diisopropylamine with one mole of the 4-carboxy thiazolidinyl 2-ethyl mercapto acetic acid prepared in Example I.

The reaction was effected in absolute alcohol. The product mixture was refluxed for one hour, filtered hot, and allowed to cool. Ethylic ether may be added in order to start crystallisation. The resulting ester was dried in a vacuum drier.

EXAMPLE III 4-carboxy thiazolidinyl 2-ethyl mercapto arginine acetate.

(Table I: compound No. 6)

This derivative is prepared by the reaction of one mole of arginine with 2 moles of the acid prepared in Example I, in solution in 30% alcohol.

The reaction mixture was refluxed for an hour, and then filtered hot and allowed to crystallise at ambient temperature.

EXAMPLE IV

2-[2-(benzimidazolyl methyl)-2-thioethyl]-thiazolidine 4-carboxylic acid.

(Table I: Compound No. 10)

Into a 100ml reactor equipped with an agitator, a bromine ampoule and a nitrogen inlet, there were introduced 66.82ml (1 mole) of freshly-distilled acrolein. The reactor was cooled to 0° C in an ice bath, and there was introduced, by the bromine ampoule, an alcoholic solution of 1 mole (164.23) of 2-mercapto benzimidazole (a solution containing 0.5ml of triethylamine), the 2-mercapto benzimidazole having been prepared according to reference CA 1763 (58) 9048g.

When the addition was complete, agitation was continued for 1 hour at ambient temperature, then there was introduced an alcoholic solution of 1 mole (156g) of chlorhydrate of cystein.

The resulting mixture was agitated for 48 hours, with the nitrogen blowing being maintained and an aqueous solution of 10% of potassium acetate (1 mole) was added.

The precipitate obtained was filtered and washed in water and alcohol.

The 2-(2-p-tolyl-2-thioethyl)thiazolidine 4-carboxylic acid (compound No. 3) was prepared by a similar method, using p-thiocresol instead of 2-mercapto benzimidazole.

F = decomposition at 180° C

EXAMPLE V 2-(2-pyridoxazolyl-2-thioethyl)thiazolidine 4-carboxylic acid.

(Table I: compound No. 11)

Into a well-agitated reactor with a nitrogen inlet there was introduced, in 60ml of absolute alcohol, 0.1 mole (13.8g) of 2-mercapto (4,5b)-oxazolo-pyridine and a few drops of triethylamine, under a nitrogen flow.

Thereafter 0.11 mole of freshly-distilled acrolein was introduced cold, through a double-jacket bromine ampoule. The resulting mixture was agitated for 8 hours, and then there was added 15.6g (0.1 mole) of a hydroalcoholic solution of chlorhydrate of cystein followed after an hour by a concentrated aqueous solution of 0.1 mole of potassium acetate.

The precipitate obtained was filtered and washed in water and alcohol. The product was recrystallised in degasified water.

EXAMPLE VI 4-carboxy thiazolidinyl-2-ethyl mercapto acetate of ethyl acid.

(Table I: compound No. 7)

In an Erlen placed in an ice bath, and under a well-ventilated hood, a solution of 0.1 mole of acrolein in 100ml of ether was introduced. With the aid of a bromine ampoule, 0.1 mole (≈11 ml) of ethylic ester of thioglycolic acid containing 0.5 ml of triethylamine was added drop by drop.

One hour after completion of the addition, there was added 0.1 mole (15.6g) of chlorhydrate of cystein in alcoholic solution. The chlorhydrate of the expected derivative, which appeared in the form of a thick oil, was precipitated by addition of 0.1 mole (10g) of potassium acetate in aqueous solution. The abundant precipitate obtained was filtered and washed in water and ether.

The product was recrystallised in a minimum of absolute alcohol.

F (Kofler): 142° C

EXAMPLE VII 2-(2-methyl-2-thioethyl) thiazolidine 4-carboxylic acid.

(Table I: compound No. 1)

An alcoholic solution cooled to 0° C and containing 0.11 mole of methyl mercaptan was prepared by blowing. 1 ml of triethylamine was added drop by drop, with the aid of an externally-cooled bromine ampoule, with nitrogen, on to 0.1 mole (7ml) of acrolein which was well agitated, at 0° C.

When the addition was complete, the mixture was left for one hour at ambient temperature, then was cycled with the aid of 0.1 mole of chlorhydrate of cystein in a hydroalcoholic solution.

The base was formed by addition of 0.1 mole (10g) of potassium acetate in aqueous solution. The mixture was then filtered. The precipitate obtained was dried and then recrystallized in hot water, under nitrogen.

F (Kofler): 169° C (decomposition).

2-(2-ethyl 2-thioethyl) thiazolidine 4-carboxylic acid was obtained in a similar manner (compound No. 2).

For both these products, production was carried out under a well-ventilated hood during the entire course of the operation, including recrystallisation.

EXAMPLE VIII 1-(acetyl2-thioethyl) thiazolidine 4-carboxylic acid.
(Table I: compound No. 9)

Into an Erlen cooled to 0° C there was placed, under $N_2$ and with agitation, 13.4 ml (0.2 mole) of acrolein. Then 0.2 mole (14.2ml) of thioacetic acid was added dropwise. The solution obtained was allowed to stand for a night, and then, under reduced pressure, the β-acetyl thio propaldehyde obtained was distilled. E/14mn = 72°–93° C.

0.11 mole of this aldehyde was added to an aqueous solution of 0.1 mole of chlorhydrate of cystein. This operation was carried out at ambient temperature, with good agitation and with nitrogen blowing. A precipitate formed after an hour.

0.1 mole of potassium acetate was added in a concentrated aqueous solution. The precipitate which formed was filtered and recrystallized in water, under nitrogen.

F (Kofler): 179° C

EXAMPLE IX

2-[(Ethoxy carbonyl methyl thio)-ethyl] thiazolidine 4-carboxylate of diisopropylamine.
(Table I: compound No. 8)

Into a 200ml reactor fitted with an agitator, a cooler and a bromine ampoule, there was placed 1 mole (279.36g) of 4-carboxy thiazolidinyl 2-ethyl mercapto acetate of ethyl acid. 50ml of absolute alcohol were added.

By means of the bromine ampoule, there was introduced slowly, with agitation, an ether solution of 1 mole of diisopropylamine. The reaction was exothermic.

After completion of the addition, the mixture was refluxed, without agitation, for an hour, and was then filtered hot and allowed to precipitate. Filtering and drying was carried out on silica gel.

F = decomposition at 80°–85° C.

EXAMPLE X 2-(2-dodecyl 2-thio-ethyl) thiazolidine 4-carboxylic acid.

(Table I: compound No. 12).

Into a 1000 ml reactor fitted with an agitator and a nitrogen inlet, there was charged 0.10 mole of dodecylmercaptan (20.24g) in 20ml of ether. By means of a bromine ampoule, there was added 0.10 mole (7ml) of acrolein containing 0.5ml of triethylamine, the mixture being violently agitated and cooled.

The agitation was continued at ambient temperature and under $N_2$ for 2 hours. There was added a hydroalcoholic solution of chlorhydrate of cystein 0.1 mole (15.7g), followed by 0.10 mole of potassium acetate in aqueous solution. The precipitate obtained ws filtered and recrystallised in absolute alcohol.

EXAMPLE XI

Analgesic Action.

This action was proved by the Siegmund test.

Reference: SIEGMUND, E. A.: CADMUS, R. A.: GOLU: "A Method for evaluating both non-narcotic and narcotic Analgesics." Pro. Soc. Exp. Biol.,1957, b,95, 729–731.

Principle: Injection of an irritant, phenylbenzoquinone (in 0.02% solution), into the peritoneum of a mouse, determination of the stretching or twisting movements (writhing syndrome), whose frequency is diminished by the preventive administration of analgesic.

the substances were given orally 30 minutes before injection of the irritant. The number of stretching movements between the 5th and 10th minute after injection of phenylbenzoquinone were counted. The percentage of animals protected was calculated. A mouse was considered protected if it executed less than five stretching movements in 5 minutes.

Results:

| Product No. | Acute Toxicity mouse PO. mg/kg. | Dose administered PO. mg/kg. | % of animals protected |
|---|---|---|---|
| 4 | >1200 | 300 | 40 |
| 5 | >1200 | 300 | 20 |
| 6 | >1200 | 300 | 20 |
| 11 | >1200 | 300 | 20 |

These products, whose toxicity is particularly low, had a clearly analgesic action at different doses.

EXAMPLE XII

Cardiovascular Action

This action was studied in a dog, anaesthetised with chloralose, its reflexogenic, cardioaortic and sinocarotidian zones being intact (normotense dog), or denervated (hypertense dog). The product to be tested was injected in the saphena vein, and the femoral arterial pressure and cardiac contractile force were recorded.

Certain derivatives of the invention have antihypertensive and hypotensive and/or cardiostimulant properties at high dosage.

Examples: Compound No. 5, whose toxicity is low (DL 50>1200 mg/kg per os) is antihypertensive and hypotensive at an intravenous dosage of 10 mg/kg.

Compound No. 10, whose toxicity is low (DL 50>1200 mg/kg per os) has, at a dosage of 20 mg/kg, clear cardiostimulant properties.

EXAMPLE XIII

Mucolytic action: measurement of the fluidising action of the bronchial secretion.
references:
"Viscosimetrie des expectorations"
Cl. MOLINA and collaborators.
"Journal Francais de Medecine et Chirurgie Thoracique"
vol. XXIII, No. 7, 1969, p. 473–758 — DOIN edition.
"La rheologie des expectorations. Materiel et Methodes"
J. M. AIACHE and collaborators. "Le poumon et le coeur"
vol. XXVI, No. 1, 1970, p. 35–49. Vigot Freres edition.
Principle:
The study of the viscosity of an expectoration is effected in vitro. In order to measure viscosity, a microviscosimeter of the BROOKFIELD type is used. With the aid of this apparatus, the resistant couple exerted on a rotor is determined. This rotor, submerged in the liquid whose viscosity is to be measured, rotates at a known constant speed.

Experimental Procedure 1.5 ml of secretion, taken to ambient temperature, was poured into a container of the viscosimeter. After 4 minutes, the temperature of the expectoration was balanced at 37° C, then the motor of the apparatus was started for 5 minutes, after which measurement was effected.

Three rotor speeds were used:
1.5 r.p.m.; 3 r.p.m., and 6 r.p.m.

The three speeds were used for each test. Firstly, the viscosity of the pure expectoration was measured, then that of the expectoration to which had been added one drop of distilled water as a solvent, and whose retained values were later used as witness values, or placebo values.

Thereafter, 1.5 ml of secretion had added to it a drop of the product at the first aqueous concentration envisaged.

The viscosity was measured at the three rotary speeds of the rotor. The same operation was repeated at the following concentrations; 1 mg/ml; 2 mg/ml and 5 mg/ml.

The reference substance was mercapto-ethane sulfonate of sodium or MISTABRON (M.E.S. Na). This substance had been studied under the same experimental conditions at a concentration of 200 mg/ml.
Results
The results are expressed in the following table:

| compound | concentration | Percentage diminution of viscosity | | |
|---|---|---|---|---|
| | mg/ml | speed r.p.m. V = 6 | speed r.p.m. V = 3 | speed r.p.m. V = 1.5 |
| 8 | 1 | 46 | 55 | 58 |
| | 2 | 47.5 | 57 | 60 |
| | 5 | 58 | 62 | 71 |
| M.E.S. Na | 200 | 55 | 65 | 66 |

Conclusions

In accordance with the doses used, and under the experimental conditions described above, compound No. 8, whose toxicity is particularly low (DL 50 = 4000 mg/kg per os in the mouse), has a mucolytic action which is comparable with and even superior to the reference substance or M.E.S. Na.

Further according to the present invention there is provided a pharmaceutical composition containing one or more of the derivatives of the invention as active ingredients. Pharmaceutical compositions intended for oral, rectal, parenteral or local administration, such as in plain or sugar-coated form, for purposes of delayed action, capsules, gelules, suppositories, solvents, syrups, injectable ampoules, creams, lotions, ointments, may be prepared in conventional manner with the excipients corresponding to the forms chosen.

By way of example, the following pharmaceutical forms have been envisaged:

EXAMPLE XIV

Pharmaceutical form: syrup

A syrup advantageously having the following composition may be used for human therapy:

| Compound No. 8 | | 5g |
|---|---|---|
| Sugared, flavoured excipient | q.s.p. | 100ml |
| 3 table spoons per day | | |

EXAMPLE XV

Pharmaceutical form: rhinological spray

| Compound No. 8 | | 2g |
|---|---|---|
| Aqueous excipient | q.s.p. | 100ml |

In 10ml ampoules with atomiser bottle for nasal sprays or pharyogeal sprays, at four sprays per day, used in drops for nasal inhalations.

EXAMPLE XVI

Pharmaceutical form: Ointment
May be used in human therapy as an ointment advantageously having the following composition:

| Compound No. 8 | 4 | g |
|---|---|---|
| sulfosalicylate of calcium and lithium | 0.25 | g |
| folic acid | 0.05 | g |
| anhydrous lanoline | 20 | g |
| Wax | 1.5 | g |
| Officinal petroleum jelly | 28.5 | g |
| Distilled water q.s.p. | 45.7 | g |

The above ointment is to be applied 2 to 4 times per day.

EXAMPLE XVII

Pharmaceutical form: Pills
Pills of the following composition may be used in human therapy:

| in human therapy: For 1 pill: | |
|---|---|
| Compound No. 8 | 0.100g |
| Kieselguhr | 0.100g |
| Sugar | 0.040g |
| Talc | 0.015g |
| Starch | 0.015g |
| Magnesium stearate | 0.015g |

Average doses are 1 to 4 pills per day.

EXAMPLE XVIII

Pharmaceutical form: gelules
Gelules of the following composition may be used in human therapy:

| For 1 gelule: | |
|---|---|
| Compound No. 8 | 0.200g |
| Doses are 2 to 3 gelules per day. | |

EXAMPLE XIX

Pharmaceutical form: suppositories
Suppositories of the following composition may be used in human therapy, rectally administered:

| For 1 suppository: | | |
|---|---|---|
| Compound No. 4 | 0.100g | |
| Excipient q.s.p. | 3 | g |

One suppository in the evening on going to bed, a second in the morning if necessary.

EXAMPLE XX

Pharmaceutical form: injectable solution
An injectable solution of the following composition may be used in human therapy:

| Compound No. 5 | 5mg |
|---|---|
| Water for injectable preparations q.s.p. | 1ml |

In I.A., I.M. and I.V. injections.

what is claimed is:
1. 2-[2-(Carboxymethylthio)ethyl]thiazolidine-4-carboxylic acid.
2. The diisopropyl ammonium salt of 2-[2-(carboxymethylthio)ethyl]thiazolidine-4-carboxylic acid.
3. The Arginine salt of 2-[2-(carboxymethylthio)ethyl]thiazolidine-4-carboxylic acid.
4. The ethyl ester of 2-[2-(carboxymethylthio)ethyl]-thiazolidine-4-carboxylic acid.
5. The di(diisopropylammonium) salt of 2-[2-(carboxymethylthio)ethyl]thiazolidine-4-carboxylic acid.
6. 2-[2-(Methylthio)ethyl]thiazolidine-4-carboxylic acid.
7. 2-[2-(Ethoxycarbonylmethylthio)ethyl]thiazolidine-4-carboxylic acid.
8. 2-[2-(Dodedecylthio)ethyl]thiazolidine-4-carboxylic acid.

* * * * *